(12) United States Patent
Lin et al.

(10) Patent No.: US 11,782,256 B2
(45) Date of Patent: Oct. 10, 2023

(54) ENDOSCOPE IMAGER AND ASSOCIATED METHOD

(71) Applicant: OmniVision Technologies, Inc., Santa Clara, CA (US)

(72) Inventors: Yi-Fan Lin, Wujie (TW); Wei-Ping Chen, New Taipei (TW); Jau-Jan Deng, Taipei (TW); Suganda Jutamulia, Berkeley, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 243 days.

(21) Appl. No.: 15/271,679

(22) Filed: Sep. 21, 2016

(65) Prior Publication Data

US 2018/0081163 A1 Mar. 22, 2018

(51) Int. Cl.
| | |
|---|---|
| *G02B 23/10* | (2006.01) |
| *A61B 1/04* | (2006.01) |
| *G02B 23/04* | (2006.01) |
| *A61B 1/06* | (2006.01) |
| *A61B 1/00* | (2006.01) |
| *H04N 23/55* | (2023.01) |
| *H04N 23/56* | (2023.01) |
| *A61B 1/05* | (2006.01) |
| *A61B 1/313* | (2006.01) |

(Continued)

(52) U.S. Cl.
CPC .......... *G02B 23/10* (2013.01); *A61B 1/00096* (2013.01); *A61B 1/00177* (2013.01); *A61B 1/051* (2013.01); *A61B 1/0623* (2013.01); *A61B 1/0676* (2013.01); *A61B 1/0684* (2013.01); *A61B 1/3137* (2013.01); *G02B 23/04* (2013.01); *G02B 23/2423* (2013.01); *G02B 23/2446* (2013.01); *G02B 23/2461* (2013.01); *G02B 23/2484* (2013.01); *H04N 23/55* (2023.01); *H04N 23/56* (2023.01); *G02B 27/283* (2013.01); *H04N 23/555* (2023.01)

(58) Field of Classification Search
USPC .......................................................... 348/68
See application file for complete search history.

(56) References Cited

U.S. PATENT DOCUMENTS

| | | | |
|---|---|---|---|
| 2005/0127820 A1* | 6/2005 | Yamazaki | ........... H01L 51/5281 313/506 |
| 2011/0213204 A1 | 9/2011 | Kuroda | |

(Continued)

OTHER PUBLICATIONS

SiP White Paper V9.0, The Next Step in Assembly and Packaging: System Level Integration in the Package (SiP), 127 pages, Jan. 2009.

*Primary Examiner* — Mikhail Itskovich
(74) *Attorney, Agent, or Firm* — COZEN O'CONNOR

(57) ABSTRACT

An endoscope imager includes a system-in-package and a specularly reflective surface. The system-in-package includes (a) a camera module having an imaging lens with an optical axis and (b) an illumination unit. The system-in-package includes (a) a camera module having an imaging lens with an optical axis and (b) an illumination unit configured to emit illumination propagating in a direction away from the imaging lens, the direction having a component parallel to the optical axis. The specularly reflective surface faces the imaging lens and forming an oblique angle with the optical axis, to deflect the illumination toward a scene and deflect light from the scene toward the camera module.

19 Claims, 11 Drawing Sheets

(51) Int. Cl.
  *G02B 23/24* (2006.01)
  *H04N 23/50* (2023.01)
  *G02B 27/28* (2006.01)

(56) References Cited

U.S. PATENT DOCUMENTS

| | | | |
|---|---|---|---|
| 2012/0031977 A1* | 2/2012 | Havens | G06K 7/10712 235/472.01 |
| 2014/0362200 A1* | 12/2014 | Kanamori | A61B 1/0638 348/70 |
| 2015/0312451 A1 | 10/2015 | Lei | |

* cited by examiner ated METHOD

BACKGROUND

An endoscope is a medical diagnostic instrument used for imaging a ventricle within a patient. It includes a flexible shaft capable of being inserted into the patient through an orifice thereof. The shaft has a tip that includes a light source and a camera for respectively illuminating and capturing images of part of the patient, such as a body cavity or an organ. The endoscope has a field of view by virtue of the camera. An endoscope with a viewing port through the end of the tip is an end-view endoscope. An endoscope with a viewing port through a side of the tip is a side-view endoscope.

FIG. 1 is a cross-sectional view of a ventricle 190 that includes a lesion 192 imaged by an end-view endoscope 110 and a side-view endoscope 120. Lesion 192 is on a ventricle sidewall 191. Ventricle 190 has a ventricle diameter 190D in the cross-section of FIG. 1, and is for example a portion of an esophagus or an intestine.

An advantage of side-view endoscope 120 is that it can image sidewalls of narrower ventricles than can end-view endoscope 110. Both endoscopes 110 and 120 have a shaft width 112. To image sidewall 191 perpendicularly, end-view endoscope 110 must bend at the tip so its width within ventricle 190 is width 114, which exceeds width 112. Width 114, which depends on a minimum bend radius of endoscope 110, places a lower limit on ventricle diameter 190D of ventricles 190 that end-view endoscope 110 can safely image or even enter.

FIG. 2 is a cross-sectional view of a prior-art side-view endoscope 200 that includes a camera 210 and a fiber-optic illuminator 220 in an enclosure 202. Endoscope 200 has a width 200W that has a lower limit constrained by bend radius 220R of fiber-optic illuminator 220. Width 200W is for example three to five times bend radius 220R. This lower limit limits the minimum diameter 190D of ventricles 190 that endoscope 200 may access.

SUMMARY OF THE INVENTION

In one embodiment, an endoscope imager includes a system-in-package and a specularly reflective surface. The system-in-package includes (a) a camera module having an imaging lens with an optical axis and (b) an illumination unit configured to emit illumination propagating in a direction away from the imaging lens, the direction having a component parallel to the optical axis. The specularly reflective surface faces the imaging lens and forms an oblique angle with the optical axis, to deflect the illumination toward a scene and deflect light from the scene toward the camera module.

In another embodiment, an endoscope imager includes a camera module, an illumination unit, and a specularly reflective surface. The camera module has an imaging lens with an optical axis. The illumination unit is (a) mounted on a substrate top surface that is substantially parallel to the optical axis, and (b) configured to emit illumination propagating substantially orthogonally to the optical axis, to illuminate a scene in the camera module's field of view. The specularly reflective surface faces the imaging lens and forms an oblique angle with the optical axis. The illumination unit is between the specularly reflective surface and the camera module, in dimension parallel to the optical axis.

In a third embodiment, a endoscopic imaging method includes steps of (i) generating, within an endoscope enclosure, a first source illumination propagating toward a distal end of the endoscope enclosure, (ii) deflecting the first source illumination such that it exits a side viewing port of the endoscope enclosure and propagates toward a scene, and (iii) deflecting light propagating from the scene and entering the endoscope enclosure through the side viewing port such that it is incident on a camera within the endoscope enclosure.

DETAILED DESCRIPTION OF THE EMBODIMENTS

Figure 1:
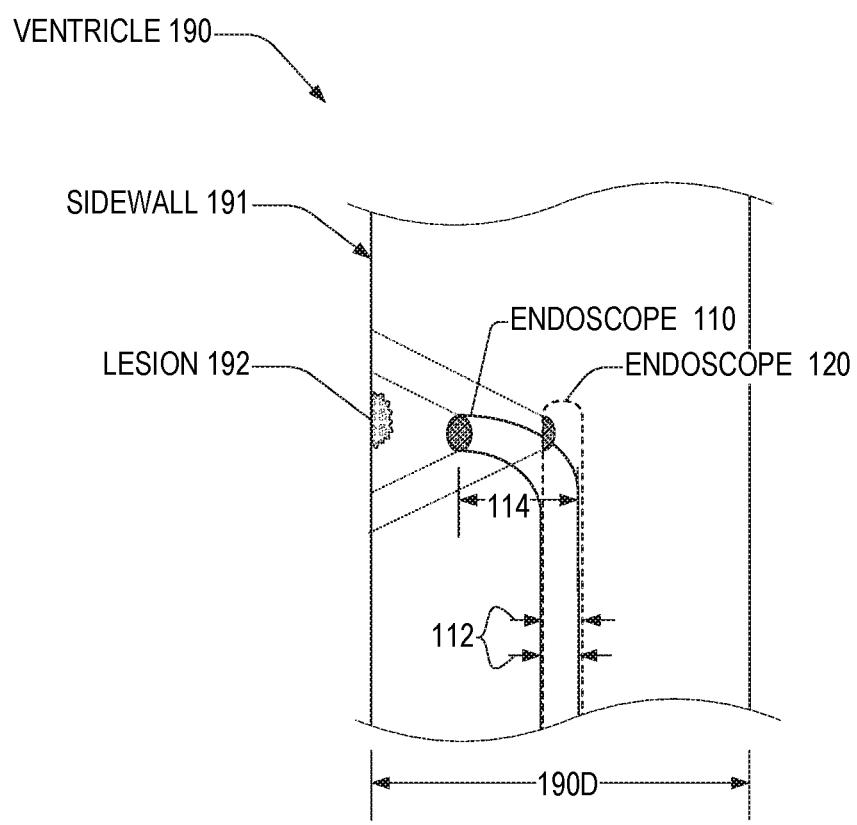
FIG. 1 is a cross-sectional view of a ventricle that includes a lesion imaged by an end-view endoscope.
Figure 2:
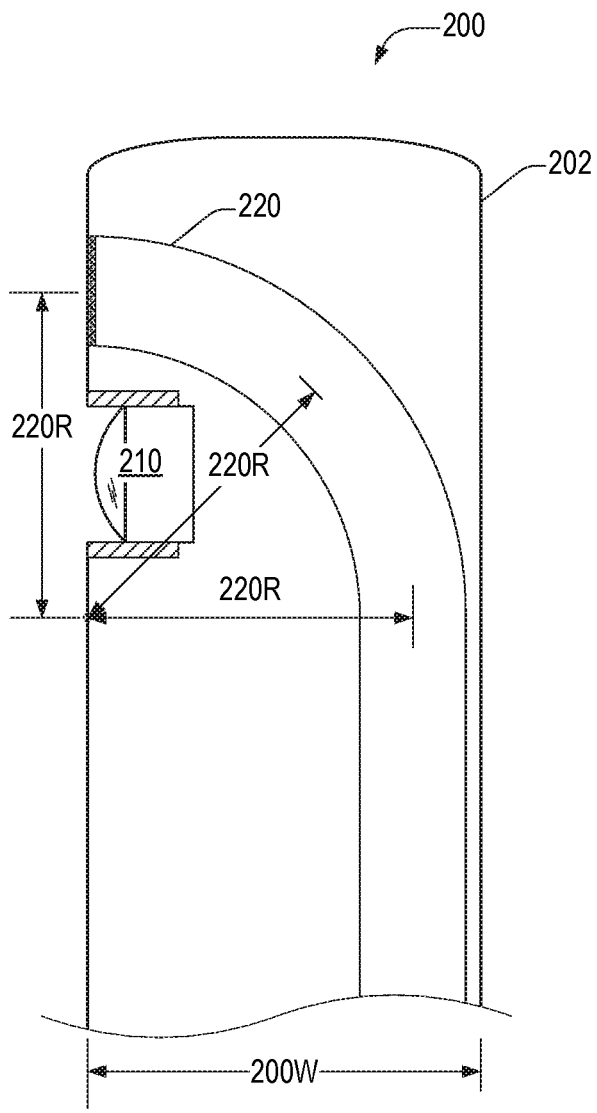
FIG. 2 is a cross-sectional view of a prior-art endoscope.
Figure 3A:
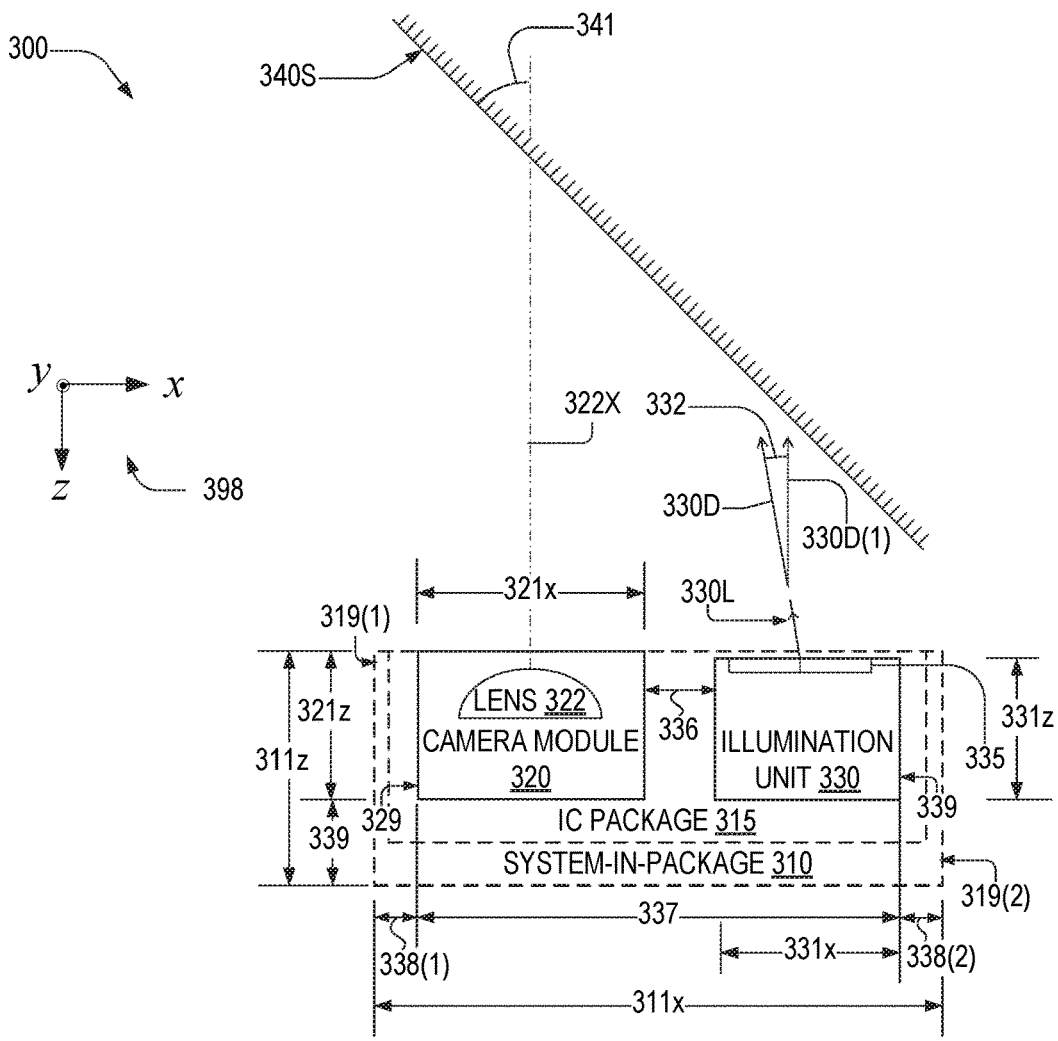
FIG. 3A is cross-sectional view and FIG. 3B is a plan view of a first endoscope imager configured for side-view endoscopy, in an embodiment.
Figure 3B:
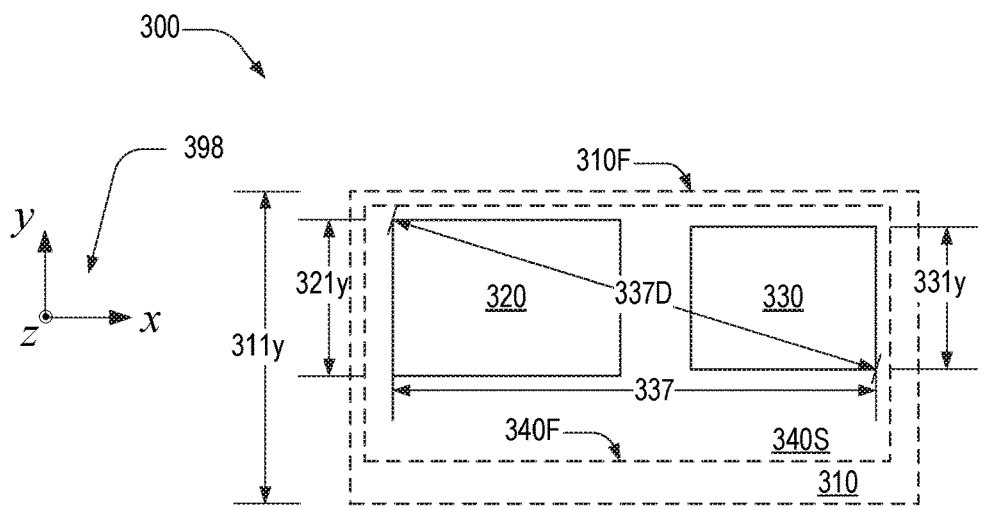

FIG. 3A is cross-sectional view and FIG. 3B is a plan view of one exemplary endoscope imager 300 that is configured for side-view endoscopy. The views of FIGS. 3A and 3B are parallel to the x-z plane and x-y plane, respectively, of a coordinate system 398. Herein, references to coordinate axes are to the x, y, and z axes of coordinate system 398, unless stated otherwise.

Endoscope imager 300 includes a camera module 320, an illumination unit 330, and a specularly reflective surface 340S that deflects output of illumination unit 330 and deflects light toward camera module 320.

Camera module 320 has an imaging lens 322 with an optical axis 322X. Specularly reflective surface 340S forms an oblique angle 341 with optical axis 322X. Angle 341 is for example 45±5°, or 45±20°. Illumination unit 330 has a light-emitting region 335 configured to emit illumination 330L, at least a portion of which propagates in a direction 330D away from imaging lens 322 and toward the specularly reflective surface 340S. Illumination 330L propagates at an angle 332 with respect to optical axis 322X, and direction 330D has a direction component 330D(1) parallel to optical axis 322X. Angle 332 may equal zero without departing from the scope hereof.

Camera module 320 and an illumination unit 330 are for example part of a system-in-package (SiP) 310 that includes an integrated circuit (IC) package 315, in which case camera module 320 and illumination unit 330 are mechanically and electrically connected to integrated circuit package 315. Integrated circuit package 315 is for example a chip-scale package, a chip-on-board package, a flip-chip package, or other integrated circuit package known in the art.

FIG. 3B shows a footprint 310F of SiP 310 and a footprint 340F of specularly reflective surface 340S. In an embodiment, footprint 340F is entirely within footprint 310F, as shown in FIG. 3B. In a different embodiment, footprint 310F is entirely within footprint 340F.

Camera module 320 has dimensions 321x, 321y, and 321z that are parallel to the x, y, and z axes respectively. In one example, dimensions 321x and 321y are each 1.2±0.3 millimeters, and dimension 321z is for example 2.4±0.5 millimeters. In another example, each dimension 321x and 321y is less than 1.5 millimeters and dimension 321z is less than 2.5 millimeters. Illumination unit 330 has dimensions 331x, 331y, and 331z that are parallel to the x, y, and z axes respectively. Dimensions 331x and 331y are each for example 1.2±0.3 millimeters and dimension 331z is less than 2.5 millimeters.

Camera module 320 and illumination unit 330 are separated by a gap distance 336 that may be at least 0.25 millimeters. In one example, gap distance 336 is between 0.25 and 0.5 millimeters. Camera module 320 and illumination unit 330 have respective outer edges 329 and 339 separated by a distance 337, in the plane of FIG. 3A, that may be less than three millimeters. Distance 337 is for example 2.7±0.1 millimeters. Camera module 320 and illumination unit 330 have a maximum edge separation 337D, which is for example between 2.7 and 3.3 millimeters.

SiP 310 has edges 319(1,2), which are, for example, edges of a PCB to which SiP 310 is mounted. Outer edges 329 and 339 are distances 338(1) and 338(2) from edges 319(1) and 319(2), respectively. Distance 338 may be at least 0.2 millimeters. SiP 310 has dimensions 311x, 311y, and 311z that are parallel to the x, y, and z axes respectively. Dimension 311x is the sum of distance 337 and distances 338(1,2). Dimension 311z is at least the larger of dimension 321z and 331z, and, in an embodiment, includes a thickness 339 of a PCB to which SiP 310 is mounted. Thickness 339 may be between 0.6 millimeters and 1.0 millimeters such that dimension 311z is between 3.1 millimeters and 3.5 millimeters. Thickness 339 may be between 0.6 millimeters and 1.0 millimeters such that dimension 311z is between 3.1 millimeters and 3.5 millimeters.

Camera module 320 may include a complementary metal-oxide semiconductor (CMOS) image sensor. Lens 322 may be formed of wafer-level imaging optics integrated with camera module 320. Without departing from the scope hereof, lens 322 may be a composite imaging objective including a plurality of optical components such as one or more lenses, filters, and/or apertures. Illumination unit 330 for example includes one or more light-emitting diodes (LEDs) and may emit polarized light, partially-polarized light, or unpolarized light. Illumination 330L may include electromagnetic radiation of at least one of ultraviolet, visible, and near-infrared wavelengths. Endoscope imager 300 may include a mirror substrate or a prism that includes specularly reflective surface 340S. Specularly reflective surface 340S may be a polarizing beam-splitting surface. Camera module 320 may be compatible with and withstand surface-mount technology (SMT) reflow soldering processes, for example, processes occurring at temperatures exceeding 250° C.

Figure 4:
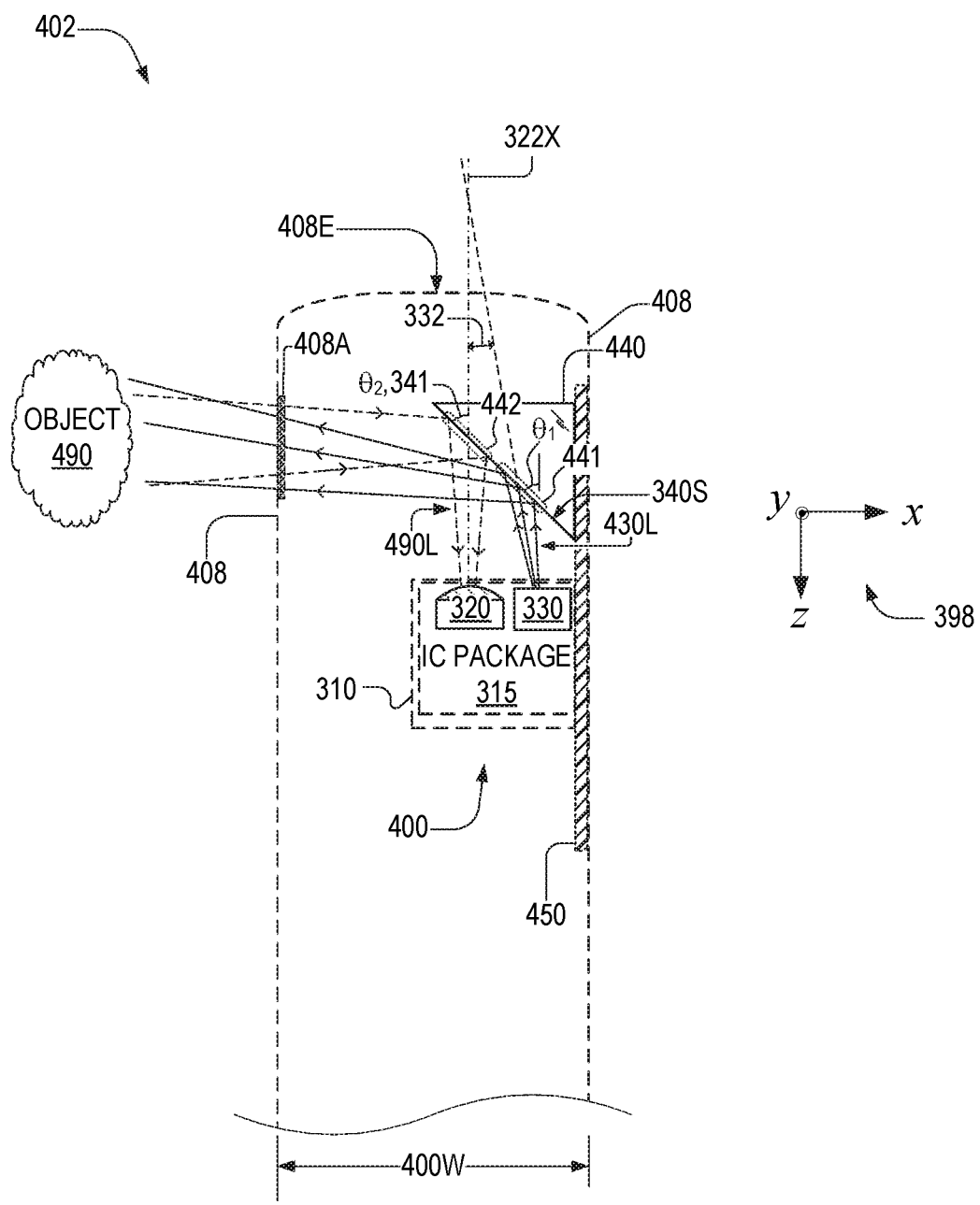
FIG. 4 is a cross-sectional view of one exemplary side-view endoscope implementing an embodiment of the endoscope imager of FIGS. 3A and 3B in an enclosure.

FIG. 4 is a cross-sectional view of one exemplary side-view endoscope 402 implementing endoscope imager 400 in an endoscope enclosure 408. Endoscope imager 400 is an example of endoscope imager 300. Endoscope imager 400 has an optical configuration that enables width 400W of enclosure 408 to be less than width 200W of prior-art endoscope 200. Width 400W may exceed width 200W without departing from the scope hereof.

Endoscope imager 400 includes camera module 320, illumination unit 330, and mirror substrate 440. Mirror substrate 440 includes specularly reflective surface 340S. Mirror substrate 440 is illustrated as a prism in FIG. 4, but may be a differently shaped substrate, such as a planar substrate, without departing from the scope hereof.

Enclosure 408 has a distal end 408E and a side viewing port 408A. During operation of endoscope imager 400, when implemented in side-view endoscope 402, illumination unit 330 emits illumination 430L, which is an example of illumination 330L. Surface 340S reflects illumination 430L toward side viewing port 408A such that it illuminates a side object 490 adjacent to endoscope imager 400 and within a field of view of camera module 320.

In response to illumination of side object 490 by illumination 430L, light 490L propagates from side object 490, enters side viewing port 408A, and reflects off of surface 340S toward camera module 320, which thereby images side object 490. Light 490L is for example illumination 430L reflected or scattered by side object 490. Alternatively, light 490L may be light generated and emitted by side object 490 in response to illumination 430L, e.g., if side object 490 includes a photoluminescent material.

Surface 340S may be a planar surface, as illustrated in FIG. 4. Alternatively, surface 340S may include two or more planar sub-surfaces that form different angles with respect to optical axis 322X. For example, illumination 430L reflects off of a first sub-surface 441 oriented at an angle $\theta_1$ with respect to optical axis 322X, where the value of angle $\theta_1$ maximizes the amount of illumination 430L that exits side viewing port 408A. Light 490L reflects off of a second sub-surface 442 oriented at an angle $\theta_2 \neq \theta_1$ with respect to optical axis 322X, wherein the value angle $\theta_2$ maximizes the amount of reflected light 490L that reaches camera module 320 and/or ensures a desired viewing direction for camera 320 through side viewing port 408A. In an embodiment, at least one of $\theta_1$ and $\theta_2$ equals angle 341 (FIG. 3A). First sub-surface 441 may include a diffractive element, such as a grating, configured to maximize illumination 430L that exits side viewing port 408A.

Endoscope imager 400 may include a substrate 450 to which camera module 320 and illumination unit 330 are mechanically attached, either directly or indirectly. Substrate 450 is for example a printed circuit board (PCB). Mirror substrate 440 may also be attached to substrate 450. Camera module 320 and illumination unit 330 may be also electrically connected to substrate 450, in which case substrate 450 is a PCB.

Figure 5A:
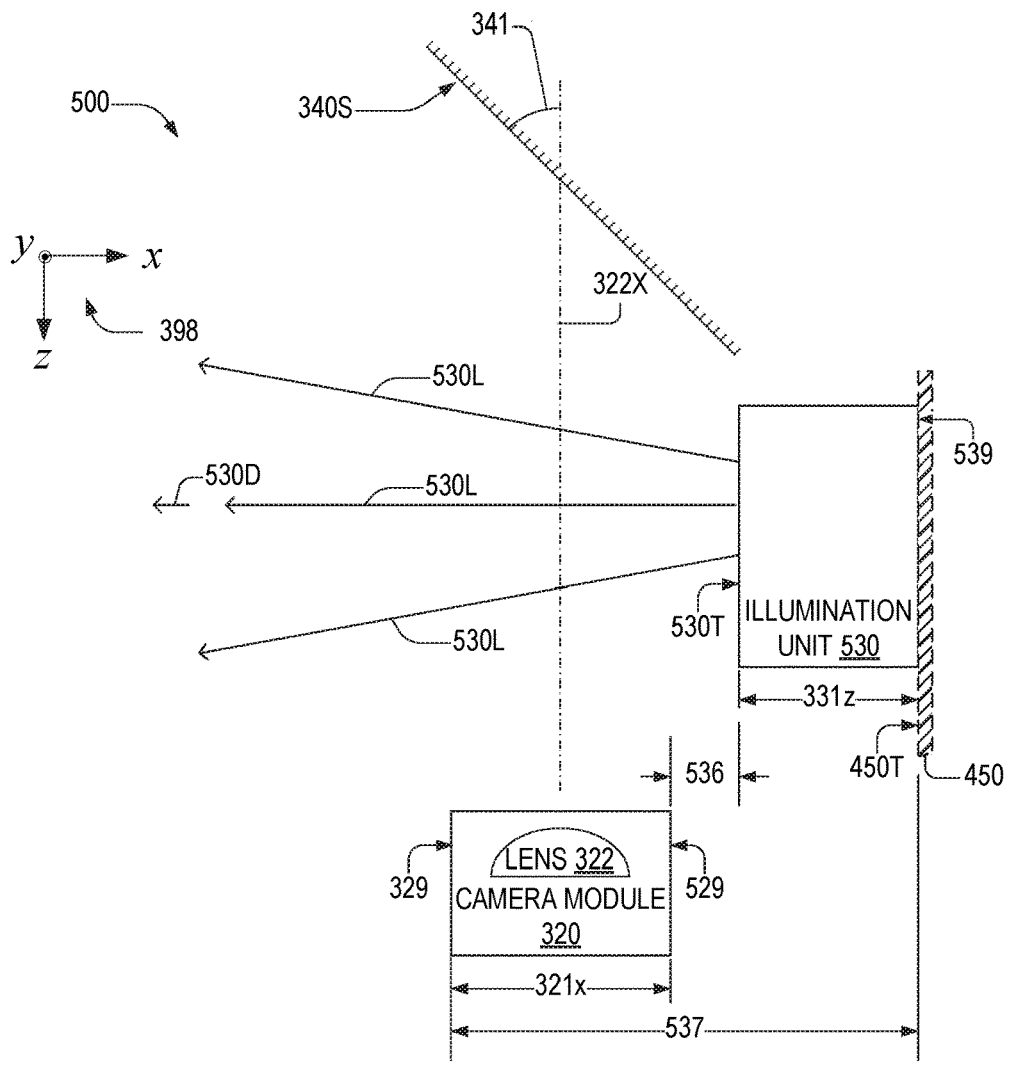
FIG. 5A is cross-sectional view and FIG. 5B is a plan view of a second endoscope imager configured for side-view endoscopy, in an embodiment.
Figure 5B:
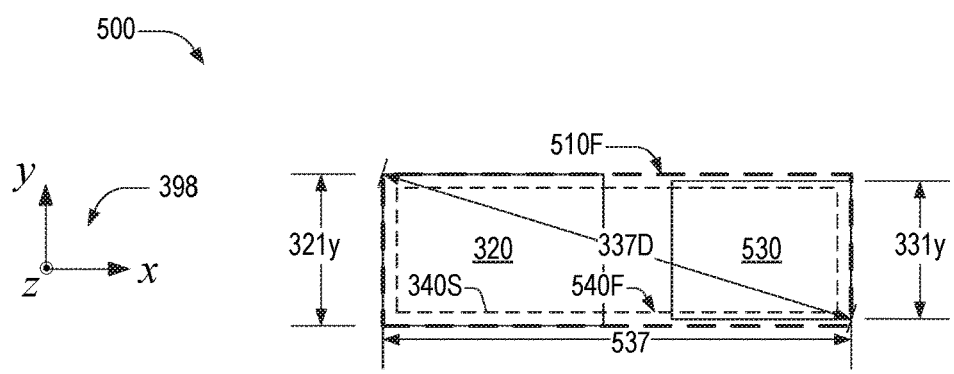

FIG. 5A is cross-sectional view and FIG. 5B is a plan view of one exemplary endoscope imager 500 that is configured for side-view endoscopy. The views of FIGS. 5A and 5B are parallel to the x-z plane and x-y plane, respectively, of a coordinate system 398

Endoscope imager 500 includes camera module 320, an illumination unit 530, and specularly reflective surface 340S. Illumination unit 530 is an example of illumination unit 330. Endoscope imager 500 may include a mirror substrate or a prism that includes specularly reflective surface 340S.

Endoscope imager 500 may also include substrate 450, to which illumination unit 530 may be mounted. Illumination unit 530 may be also electrically connected to substrate 450, in which case substrate 450 is a PCB. Illumination unit 530 is configured to emit illumination 530L propagating in an average direction 530D substantially perpendicular to optical axis 322X, to within ±5 degrees for example. Camera module 320 and illumination unit 530 have respective edges 329 and 539, which are separated by a distance 537 that is the sum of dimensions 321x and 331z and a gap distance 536 between a side surface 529 of camera module 320 and a top surface 530T of illumination unit 530. Gap distance 536 is for example less than half of dimension 321x such that endoscope imager 500 is compact.

Substrate 450 has a top surface 450T that is substantially parallel to the optical axis 322X, to within ±5 degrees for example, to enable illumination 530L to reflect off of objects in the field of view of camera module 320 located, in direction 530D, up to fifty millimeters from optical axis 322X.

FIG. 5B shows a rectangular footprint 510F (of camera module 320 and illumination 530) and a footprint 540F of specularly reflective surface 340S. In an embodiment, footprint 540F is entirely within footprint 510F, as shown in FIG. 5B. In a different embodiment, footprint 510F is entirely within footprint 540F. In endoscope imager 500, camera module 320 and illumination unit 530 have maximum edge separation 337D of similar size to maximum edge separation 337D of endoscope imager 300.

Figure 6:
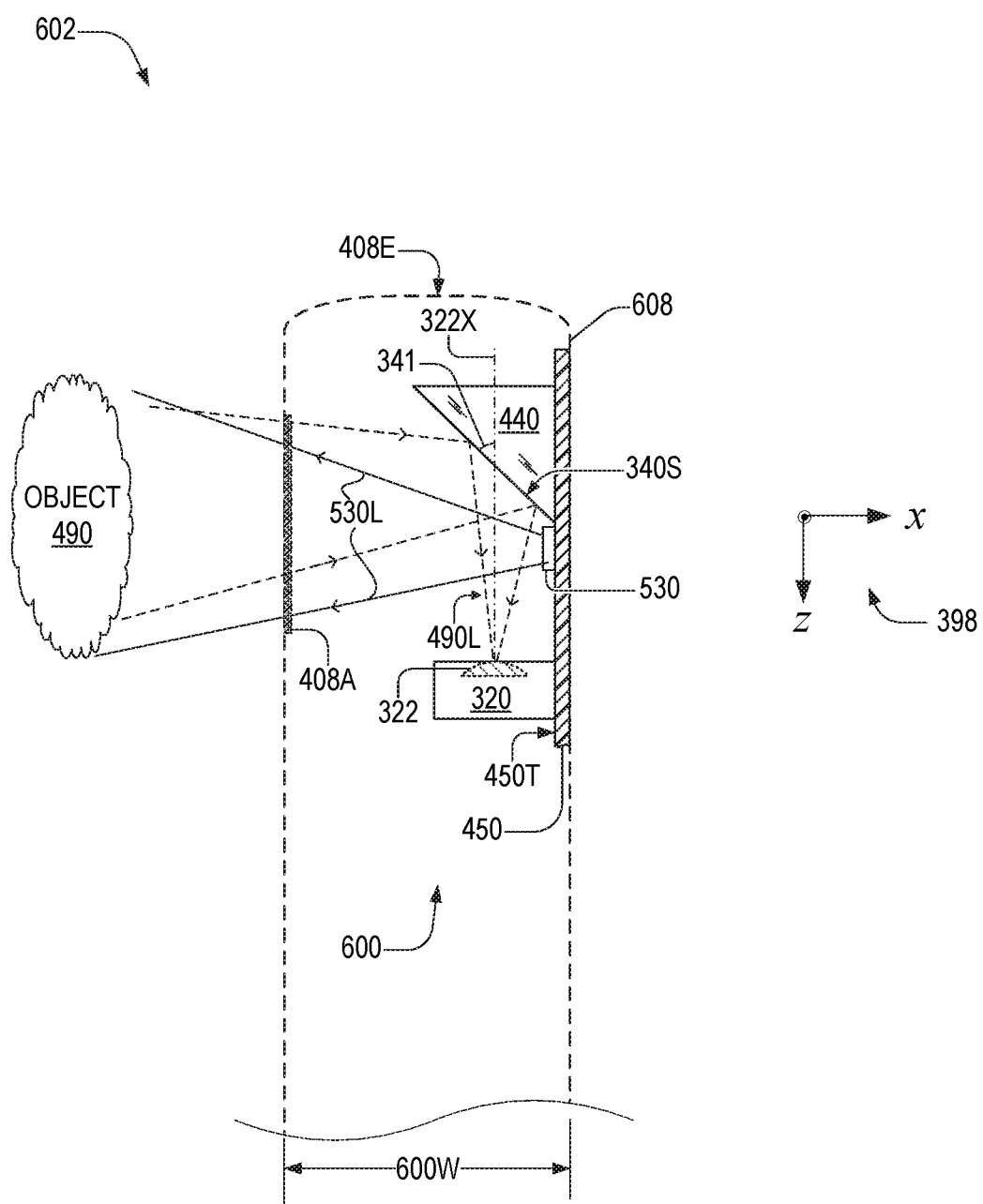
FIG. 6 is a cross-sectional view of one exemplary side-view endoscope implementing an embodiment of the endoscope imager of FIGS. 5A and 5B in an enclosure.

FIG. 6 is a cross-sectional view of a side-view endoscope 602 implementing an endoscope imager 600 in an enclosure 608. Endoscope imager 600 is an example of endoscope imager 500. Depending on the spatial dimensions of illumination unit 530, its placement on substrate 450 rather than next to camera module 320 may enable endoscope imager 600 to have a width 600W that is smaller than width 400W. Enclosure 608 has distal end 408E and a side viewing port 408A. Endoscope imager 600 is configured to illuminate and image side object 490 through side viewing port 408A.

Figure 7:
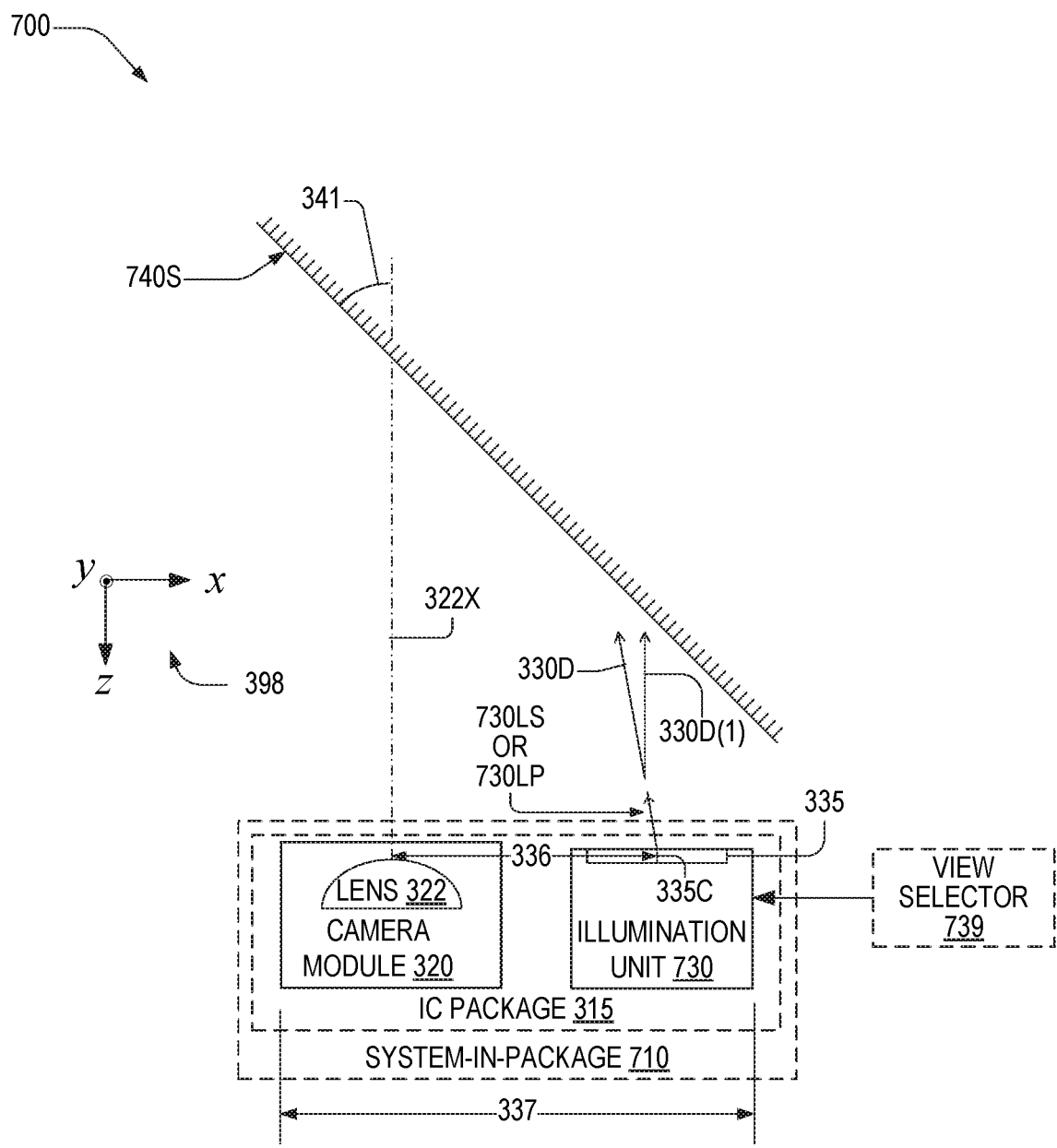
FIG. 7 is a cross-sectional view of a third endoscope imager configured for both side-view endoscopy and end-view endoscopy, in an embodiment.

FIG. 7 illustrates, in cross sectional view, one exemplary multi-view endoscope imager 700 configured for both side-view endoscopy and end-view endoscopy. Endoscope imager 700 includes camera module 320, an illumination unit 730, and a polarizing beam-splitting surface 740S. Illumination unit 730 and polarizing beam-splitting surface 740S are examples of illumination unit 330 and specularly reflective surface 340S, respectively.

Camera module 320 and illumination unit 730 are for example part of a SiP 710 that includes integrated circuit package 315, in which case camera module 320 and illumination unit 730 are mechanically and electrically connected to integrated circuit package 315.

Illumination unit 730 is capable of nonsimultaneously outputting (a) light having a first polarization state and (b) light having a second polarization state that is orthogonal to the first polarization state. The first and second polarization states may be mutually orthogonal linear polarization states, mutually orthogonal circular polarization states, or mutually orthogonal elliptical polarization states. The polarization purity of the first and second linear polarization states is, for example, 200:1 to avoid cross-talk between the multiple views of endoscope imager 700.

For example, illumination unit 730 is capable of nonsimultaneously outputting s-polarized illumination 730LS and p-polarized illumination 730LP, where s and p polarizations are, respectively, perpendicular to and parallel to the x-z plane of coordinate system 398. Polarizing beam-splitting surface 740S transmits p-polarized illumination 730LP and reflects s-polarized illumination 730LS.

Endoscope imager 700 may also include a view selector 739 that is communicatively coupled to illumination unit 730 and capable of switching the output polarization thereof. View selector 739 is for example controlled by a user-interface and may be integrated into illumination unit 730. View selector 739 may be part of SiP 710.

Figure 8:
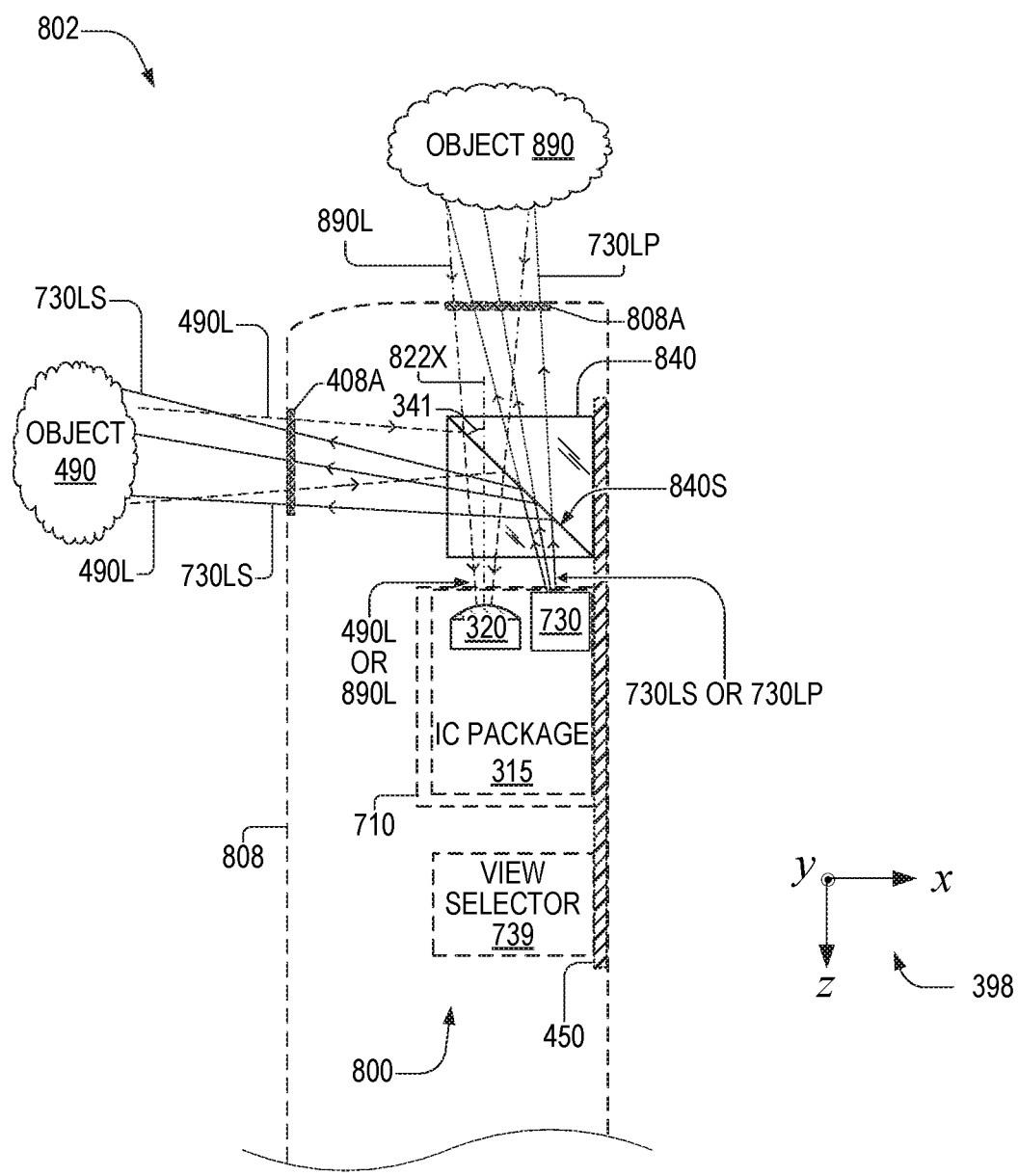
FIG. 8 is a cross-sectional view of one exemplary multi-view endoscope implementing an embodiment of the endoscope imager of FIG. 7 in an enclosure.

FIG. 8 is a cross-sectional view of one exemplary multi-view endoscope 802 implementing an endoscope imager 800 in an enclosure 808. Endoscope imager 800 is an example of endoscope imager 700. Enclosure 808 includes a distal viewing port 808A and side viewing port 408A. Endoscope imager 800 includes camera module 320, illumination unit 730, and a polarizing beamsplitter 840. Polarizing beamsplitter 840 includes polarizing a beam-splitting surface 840S, which is an example of polarizing beam-splitting surface 740S.

Endoscope imager 800 may include substrate 450 to which camera module 320 and an illumination unit 730 are mechanically attached, either directly or indirectly. Polarizing beamsplitter 840 may also be attached to substrate 450. Camera module 320 and illumination unit 730 may be also electrically connected to substrate 450, in which case substrate 450 is a PCB.

When illumination unit 730 emits s-polarized illumination 730LS, illumination 730LS reflects off of polarizing beam-splitting surface 840S and propagates through side viewing port 408A toward side object 490. Side object 490 emits light 490L, for example a reflected portion of illumination 730LS or light generated by side object 490 in response to illumination 730LS, which is transmitted through side viewing port 408A and reflected off of beam-splitting surface 840S toward camera module 320, which thereby images side object 490.

When illumination unit 730 emits p-polarized illumination 730LP, illumination 730LP is transmitted by polarizing beam-splitting surface 840S and propagates through distal viewing port 808A toward a distal object 890. Distal object 890 emits light 890L, for example a reflected portion of illumination 730LP or light generated by distal object 890 in response to illumination 730LP, which is transmitted through distal viewing port 808A and polarizing beamsplitter 840 toward camera module 320, which thereby images distal object 890.

Figure 9:
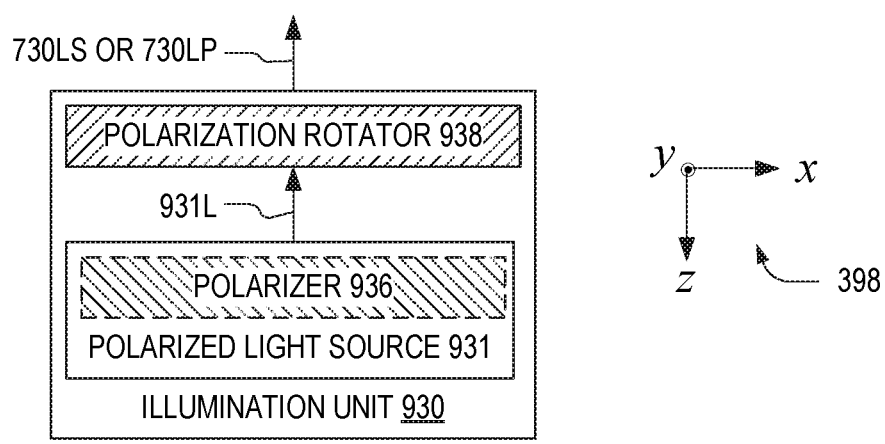
FIG. 9 is a schematic diagram of a first exemplary illumination unit of the endoscope imager of FIG. 7.

FIG. 9 is a schematic diagram of an illumination unit 930, which is an example of illumination unit 730. Illumination unit 930 includes a polarized light source 931, and a polarization rotator 938. Light source 931 for example includes an LED and a polarizer 936. Polarization rotator 938 is for example an achromatic half-wave plate with an electronically-controlled crystal-axis rotation. Alternatively, polarization rotator 938 includes active optical components such as a liquid crystal or magneto-optic crystal capable of operating as a switchable half-wave plate.

When polarization rotator 938 is in a first configuration, illumination unit 930 emits illumination 730LS. When polarization rotator 938 is in a second configuration, polarization rotator 938 rotates the polarization state of incident light 931L such that illumination unit 930 emits illumination 730LP.

Figure 10:
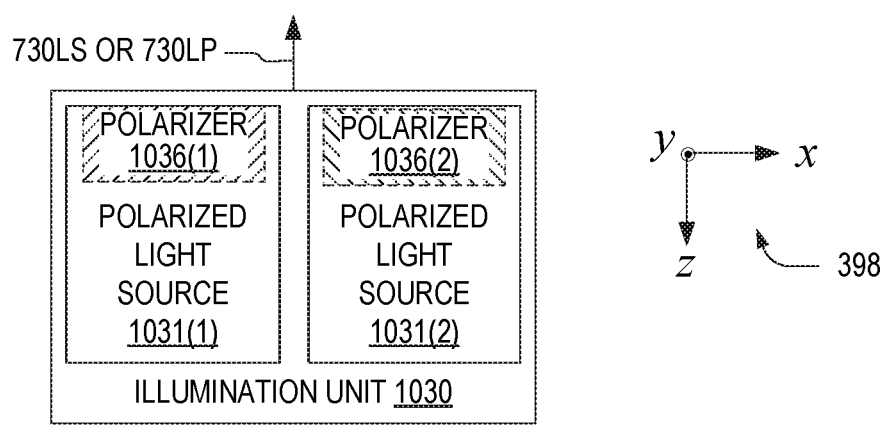
FIG. 10 is a schematic diagram of a second exemplary illumination unit of the endoscope imager of FIG. 7.

FIG. 10 is a schematic diagram of an illumination unit 1030, which is another example of illumination unit 730. Illumination unit 1030 includes s-polarized light source 1031(1) and p-polarized light source 1031(2) that emit, respectively, s-polarized light and p-polarized light as described above with respect to coordinate system 398. Each polarized light source 1031 may include respective linear polarizer 1036(1) and 1036(2) oriented orthogonal to each other. Alternatively, polarized light sources 1031(1) and 1031(2) are each polarized light sources, such as polarized LED, which emits linearly polarized light without use of a linear polarizer.

When illumination unit 1030 is in a first configuration, s-polarized light source 1031(1) is on and p-polarized light source 1031(2) is off, such that illumination unit 1030 emits illumination 730LS. When illumination unit 1030 is in a second configuration, s-polarized light source 1031(1) is off and p-polarized light source 1031(2) is on, such that illumination unit 1030 emits illumination 730LP.

Illumination unit 1030 may include more than two polarized light sources 1031. For example, illumination unit 1030 may include an M×N array of polarized light sources 1031 $(i,j)$, where $i=(1, 2, \ldots, M)$, $j=(1, 2, \ldots, N)$. Whether a polarized light source $1031(i,j)$ transmits s-polarized light or p-polarized light may depend on the parity of quantity (i+j), that is, whether (i+j) is odd or even. For example, the polarized light source 1031 at position (i,j) in the M×N array transmit s-polarized light if (i+j) is even, and transmits p-polarized light if (i+j) is odd. Such an array of polarized light sources $1031(i,j)$, ensures that both polarization outputs of illumination unit 1030 (730LS and 730LP) propagate along essentially the same path between illumination unit 730 and polarizing beamsplitter 840.

When such an illumination unit 1030 is in a first configuration, s-polarized light sources $1031(i,j)$ are on and p-polarized light sources $1031(i,j)$ are off, such that illumination unit 1030 emits illumination 730LS. When illumination unit 1030 is in a second configuration, s-polarized light sources $1031(i,j)$ are off and p-polarized light sources $1031(i,j)$ are on, such that illumination unit 1030 emits illumination 730LP.

Figure 11:
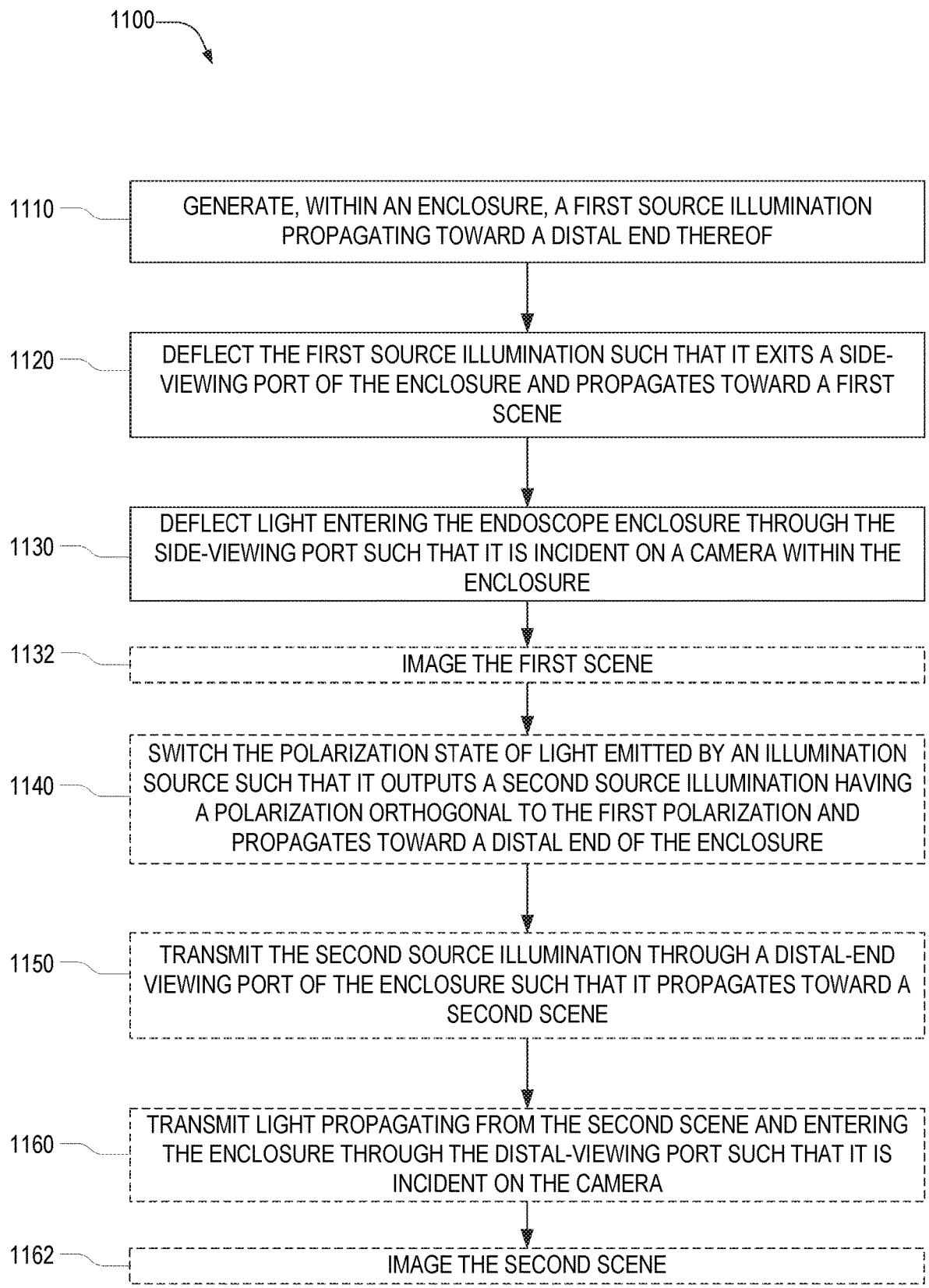
FIG. 11 is a flow chart illustrating a method for imaging a scene outside of an enclosure, in an embodiment.

FIG. 11 is a flow chart illustrating an endoscopic imaging method 1100. In one embodiment, method 1100 performs side-view endoscopy. In another embodiment, method 1100 performs end-view endoscopy. Method 1100 is suitable for non-endoscopic applications without departing from the scope hereof.

In step 1110, method 1100 generates, within an enclosure, a first source illumination propagating toward a distal end of the enclosure. In one example of step 1110, illumination unit 330 or 530 generates illumination 330L or 530L, respectively, which propagates toward distal end 408E. In another example of step 1110, illumination unit 730 of endoscope imager 800 generates source illumination 730LS, which propagates toward a distal end of enclosure 808.

In step 1120, method 1100 deflects the first source illumination such that it exits a side viewing port of the enclosure and propagates toward a first scene. In one example of step 1120, specularly reflective surface 340S reflects illumination 330L or 550L toward side-viewing port 408A. In another example of step 1120, polarizing beam-splitting surface 840S deflects source illumination 730LS toward side viewing port 408A and side object 490.

In step 1130, method 1100 deflects light propagating from the first scene and entering the enclosure through the side viewing port such that the deflected light is incident on a camera within the enclosure. In one example of step 1130, specularly reflective surface 340S deflects light 490L propagating from side object 490 such that light 490L is incident on camera module 320. In another example of step 1130, polarizing beam-splitting surface 840S deflects light 490L propagating from side object 490 such that light 490L is incident on camera module 320.

Step 1132 is optional. In step 1132, method 1100 images the first scene. In an example of step 1132, camera module 320 images side object 490.

In an embodiment of method 1100, the first source illumination has a first polarization and be generated by an illumination unit inside the enclosure. In this embodiment, the first source illumination is for example source illumination 730LS generated by illumination unit 730. This embodiment of method 1100 may also include steps 1140, 1150, and 1160.

In step 1140, method 1100 switches the polarization state of light emitted by the illumination unit such that it outputs a second source illumination having a polarization orthogonal to the first polarization and propagates toward a distal end of the enclosure. In an example of step 1140, illumination unit 730 is switched from generating source illumination 730LS to source illumination 730LP which propagates toward distal viewing port 808A. Step 1140 may utilize illumination unit 930 or 1030.

In step 1150, method 1100 transmits the second source illumination through a distal-end viewing port of the enclosure such that it propagates toward a second scene. In an example of method 1100, polarizing beam-splitting surface 840S transmits source illumination 730LP toward distal viewing port 808A and distal object 890.

In step 1160, method 1100 transmits light propagating from the second scene and entering the enclosure through the distal-viewing port such that it is incident on the camera. In an example of step 1160, polarizing beam-splitting surface 840S transmits light 890L propagating from distal object 890 such that light 890L is incident on camera module 320.

Step 1162 is optional. In step 1162, method 1100 images the second scene. In an example of step 1162, camera module 320 images distal object 890.

Combinations of Features:

Features described above as well as those claimed below may be combined in various ways without departing from the scope hereof. The following examples illustrate some possible, non-limiting combinations:

(A1) An endoscope imager includes a system-in-package and a specularly reflective surface. The system-in-package includes (a) a camera module having an imaging lens with an optical axis and (b) an illumination unit. The specularly reflective surface faces the imaging lens and forms an oblique angle with the optical axis. The illumination unit is configured to emit light propagating in a direction away from the imaging lens and toward the specularly reflective surface, wherein the direction has a component parallel to the optical axis.

(A2) In the endoscope imager denoted by (A1), the system-in-package may also include an integrated circuit package, both the camera module and the illumination unit being mechanically and electrically connected thereto.

(A3) In any of the endoscope imagers denoted by one of (A1) and (A2), the specularly reflective surface may be the most proximate material interface to the camera module along the optical axis.

(A4) In any of the endoscope imagers denoted by one of (A1) through (A3), the specularly reflective surface may be a surface of a polarizing beamsplitter.

(A5) In any of the endoscope imagers denoted by one of (A1) through (A4), the illumination unit may be adapted to nonsimultaneously output (a) first light having a first polarization state and (b) second light having a second polarization state that is orthogonal to the first polarization state.

(A6) In the endoscope imager denoted by (A5), the illumination unit may include a light source and, between the light source and the polarizing beamsplitter, a polarizer and a polarization rotator, to nonsimultaneously generate the first light and the second light.

(A7) In the endoscope imager denoted by (A5), the illumination unit may include two light sources to generate the first light and the second light, respectively.

(A8) In any of the endoscope imagers denoted by one of (A1) through (A7), the camera module and the illumination unit may be compatible with a surface-mount technology reflow soldering process.

(A9) In any of the endoscope imagers denoted by one of (A1) through (A8), the oblique angle may be between forty and fifty degrees.

(A10) In any of the endoscope imagers denoted by one of (A1) through (A9), a minimum distance between the camera module and the illumination unit in a direction perpendicular to the optical axis may be less than 0.5 millimeters.

(A11) In any of the endoscope imagers denoted by one of (A1) through (A9), a maximum distance between the camera module and the illumination unit in a direction perpendicular to the optical axis may be less than 3.3 millimeters.

(A12) An endoscope includes an enclosure and, located therein, an any of the endoscope imagers denoted by one of (A1) through (A11).

(B1) An endoscope imager includes a camera module, an illumination unit, and a specularly reflective surface. The camera module has an imaging lens with an optical axis. The illumination unit is (a) mounted on a substrate top surface that is substantially parallel to the optical axis, and (b) configured to emit illumination propagating substantially orthogonally to the optical axis, to illuminate a scene in the camera module's field of view. The specularly reflective surface faces the imaging lens and forms an oblique angle with the optical axis. The illumination unit is between the specularly reflective surface and the camera module, in dimension parallel to the optical axis.

(B2) In the endoscope imagers denoted by (B1), the specularly reflective surface may be the most proximate material interface to the camera module along the optical axis.

(B3) In an endoscope imager denoted by one of (B1) and (B2), the oblique angle may be between forty and fifty degrees.

(B4) In any endoscope imager denoted by one of (B1) through (B3), a distance between a side surface of the camera module and a plane containing a top surface of the illumination unit, in a first direction perpendicular to the optical axis, may be less than half a width of the camera module in the first direction.

(C1) An endoscopic imaging method includes steps of (i) generating, within an endoscope enclosure, a first source illumination propagating toward a distal end thereof, (ii) deflecting the first source illumination such that it exits a side viewing port of the endoscope enclosure and propagates toward a first scene, and (iii) deflecting light propagating from the first scene and entering the endoscope enclosure through the side viewing port such that it is incident on a camera within the endoscope enclosure.

(C2) In the method denoted by (C1), the first source illumination may have a first polarization and be generated by an illumination unit inside the endoscope enclosure.

(C3) The method denoted by (C2) may further include switching the polarization state of light emitted by illumination unit such that it outputs a second source illumination having a polarization orthogonal to the first polarization and propagating toward a distal end of the endoscope enclosure. The method denoted by (C2) may also include transmitting the second source illumination through a distal-end viewing port of the endoscope enclosure such that it propagates toward a second scene. The method denoted by (C2) may also include transmitting light propagating from the second scene and entering the endoscope enclosure through the distal-viewing port such that it is incident on the camera.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An endoscope imager comprising:
    a system-in-package including
        (a) a camera module having (i) an image sensor, (ii) an imaging lens distinct from the image sensor, including a convex surface, and having an optical axis intersecting the image sensor, and (iii) a field of view defined by size of the image sensor and distance between the image sensor and the imaging lens;
        (b) an illumination unit configured to emit illumination propagating in a direction away from the imaging lens, the direction having a component parallel to the optical axis,
        (c) an integrated circuit package mechanically and electrically connected to both the camera module and the illumination unit; and
    a specularly reflective surface facing the camera module and forming an oblique angle with the optical axis, the specularly reflective surface being configured to reflect the illumination toward a scene and reflect light from the scene toward the camera module,
    the image sensor and the imaging lens being on a same side of the specularly reflective surface, the imaging lens being between the specularly reflective surface and the image sensor.

2. The endoscope imager of claim 1, the specularly reflective surface being the most proximate material interface to the camera module along the optical axis.

3. The endoscope imager of claim 1, the specularly reflective surface being a surface of a polarizing beamsplitter.

4. The endoscope imager of claim 3, the illumination unit being adapted to nonsimultaneously output (a) first light having a first polarization state and (b) second light having a second polarization state that is orthogonal to the first polarization state.

5. The endoscope imager of claim 4, the illumination unit comprising a light source and, between the light source and the polarizing beamsplitter, a polarizer and a polarization rotator, to nonsimultaneously generate the first light and the second light.

6. The endoscope imager of claim 4, the illumination unit comprising two light sources to generate the first light and the second light, respectively.

7. The endoscope imager of claim 1, the oblique angle being between forty and fifty degrees.

8. The endoscope imager of claim 1, a minimum distance between an edge of the camera module and an edge of the illumination unit in a direction perpendicular to the optical axis being less than 0.5 millimeters.

9. The endoscope imager of claim 1, a maximum distance between an edge of the camera module and an edge of the illumination unit in a direction perpendicular to the optical axis being less than 3.3 millimeters.

10. An endoscope comprising an enclosure and, located therein, the endoscope imager of claim 1, the enclosure including a side-viewing port that (i) faces the specularly reflective surface and (ii) transmits the light from the scene to the specularly reflective surface.

11. An endoscope imager comprising:
a camera module having (a) an image sensor, (b) an imaging lens distinct from the image sensor, including a convex surface, and having an optical axis intersecting the image sensor, and (c) a field of view defined by size of the image sensor and distance between the image sensor and the imaging lens;
an illumination unit (a) mounted on a substrate top surface that is substantially parallel to the optical axis, and (b) configured to emit illumination propagating substantially orthogonally to the optical axis, to illuminate a scene in the camera module's field of view; and
a specularly reflective surface facing the imaging lens and forming an oblique angle with the optical axis, to reflect light from the scene toward the camera module, the image sensor and the imaging lens being on a same side of the specularly reflective surface,
the illumination unit being between the specularly reflective surface and the camera module, in dimension parallel to the optical axis.

12. The endoscope imager of claim 11, the specularly reflective surface being the most proximate material interface to the camera module along the optical axis.

13. The endoscope imager of claim 11, the oblique angle being between forty and fifty degrees.

14. The endoscope imager of claim 11, a distance between a side surface of the camera module and a plane containing a top surface of the illumination unit, in a first direction perpendicular to the optical axis, being less than half a width of the camera module in the first direction.

15. The endoscope imager of claim 1, the illumination unit configured to emit illumination direction away from the imaging lens and toward the specularly reflective surface.

16. The endoscope imager of claim 11, the illumination unit including a light-emitting diode, and further comprising:
an endoscope enclosure; and
a substrate located inside the endoscope enclosure and having the substrate top surface on which the illumination unit is mounted;
the entirety of the illumination unit being inside the endoscope enclosure.

17. The endoscope imager of claim 5, the polarization rotator including an achromatic half-wave plate.

18. The endoscope imager of claim 5, the polarization rotator including an active optical component.

19. The endoscope imager of claim 18, the active optical component being one of a liquid crystal and magneto-optic crystal.

* * * * *